United States Patent [19]

Franco et al.

[11] Patent Number: 4,738,958
[45] Date of Patent: Apr. 19, 1988

[54] ANSAMYCIN ANTIBIOTIC AND ITS USE AS A MEDICAMENT

[75] Inventors: Christopher M. M. Franco; Goukanapalli C. S. Reddy; Triptikumar Mukhopadhyay; Bimal N. Ganguli, all of Bombay, India; Hans-Wolfram Fehlhaber, Idstein, Fed. Rep. of Germany

[73] Assignee: Hoechst Aktiengesellschaft, Fed. Rep. of Germany

[21] Appl. No.: 846,945

[22] Filed: Apr. 1, 1986

[30] Foreign Application Priority Data

Apr. 3, 1985 [DE] Fed. Rep. of Germany ....... 3512194

[51] Int. Cl.$^4$ ............... C07D 227/087; A61K 31/395; C12P 17/10
[52] U.S. Cl. .................................... 514/183; 540/461; 435/121; 435/886
[58] Field of Search .......................... 540/461; 514/183

[56] References Cited

PUBLICATIONS

The Journal of Antibiotics, vol. 38, No. 7, pp. 948–951, Jul. 1985, A New Ansamycin Antibiotic, Naphthomycin H from a Streptomyces Species Y-83,40369.

Primary Examiner—Robert T. Bond
Attorney, Agent, or Firm—Finnegan, Henderson, Farabow, Garrett & Dunner

[57] ABSTRACT

The present invention relates to the compound naphthomycin H of the formula I

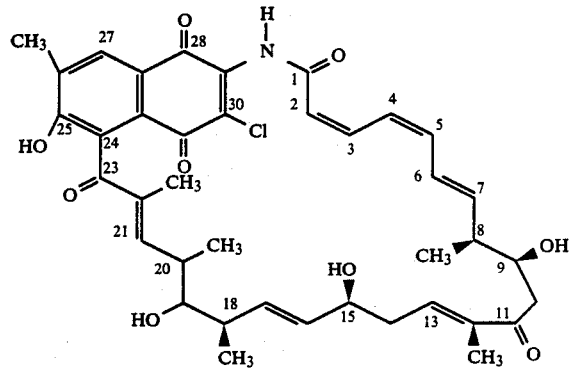

and to a microbiological process for its preparation. The compound is active against Gram-positive bacteria and fungi and can be used as an antibiotic.

3 Claims, No Drawings

ANSAMYCIN ANTIBIOTIC AND ITS USE AS A MEDICAMENT

The present invention relates to a new ansamycin antibiotic which is called naphthomycin H and to a process for its preparation from a microorganism which is called Streptomyces Y-8340369 (DSM 3278).

It is known that ansamycin antibiotics are produced by various species of Streptomyces, Nocardia and Micromonospora. It has been reported of ansamycin antibiotics from the family of naphthomycins that they are produced by various species of Streptomyces. They are also described in the literature. Ansamycin antibiotics are of importance in medicine as antibacterial agents, for controlling tumors in cancer treatment and they can also be used in agriculture to control phytopathogenic fungi. Various ansamycins have been described to date, including rifamycin which is used clinically for the treatment of tuberculosis.

Ansamycins are described in Antibiot. Ann. 1958–60, 262 (1960); Pure Appl. Chem. 7, 551 (1963), Fortschr. Chem. Org. Naturst. 33, 231-307 (1976); J. Amer. Chem. 92, 7591 (1970), 93, 6275 (1971); J. Antibiotics 23, 442 (19 and 24, 810 (1971); Accounts of Chemical Research 5, (1972); Helv. Chim. Acta 56, 2279-2287 (1973); Topics in Current Chemistry 72, 21-49 (1977) and in "Topics in Antibiotic Chemistry", Volume I, pages 93-217, Sammes P. G. (Editor), London (1977).

Rifamycins are described in Farmace Ed. Sci. 14, 146 (1959); 15, 228 (1960) and 16, 165 (1961); Prog. Indust. Microbiol. 6, 21 (1967); Arzneimittel-Forsch. 21, 1907 (1971) and U.S. Pat. Nos. 2,999,048, 3,884,763 and 4,013,789.

Tolypomycins are described in J. Antibiotics 31, 1195 (1975) and 25, 11 (1972) and in German Pat. No. 2,015,076.

Halomycins are described in Antimicrobial Agents and Chemotherapy 1967, 435–441 and J. Antibiotics 30, 625 (1977).

Streptovaricins are described in Ann. Rev. Tuberc. Pulm. Dis. 75, 576-583, (1957); J. Antibiotics 21, 204 (1968) and 25, 71–73 (1972); and Amer. Chem. Soc. 93, 6273 (1971).

Of the naphthomycin antibiotics, naphthomycin A is described in Arch. Mikrobiol. 65, 303-317 (1969); J. Antibiotics 28, 85-86 (1975) and 32, 167 (1979), and naphthomycins B and C are described in J. Antibiotics 36, 484-492 (1983). Actamycin is described in Tetrahed. Lett. 22, 1145-1148 (1981) and 22, 1149-1152 (1981).

Furthermore, there is a summary of ansamycin antibiotics in "Index of Antibiotics from Actinomycetes", Hamao Umezawa (Chief Editor) volume I, pages 218, 564–566 and 624, Univ. Park Press, State College, Pennsylvania, USA (1967) and volume II, pages 414, 446–450, 735, 897–905, 984–985, 952–954, 995–996 and 1116, Univ. Park Press Baltimore, USA (1978).

Furthermore, there is an index of ansamycins on pages 451-491 of the "CRS Handbook of Antibiotic Compounds", volume II, Microcyclic Lactone (Lactam) Antibiotics, James Berdy (Author), CRC Press Inc., Boca Raten, Fla., USA (1980).

The text book "Antibiotics", volume III, edited by J. W. Corceran and Fred E. Hahn, published by Springer, New York, USA (1975) gives a review of "Rifomycin and Other Ansamycins" by W. Wehrli and M. Staehlin on pages 252-268, while a review of the "Biosynthesis of Ansamycins" by G. Lancini and M. Grandi is to be found on pages 12–40 of volume IV, edited by J. W. Corceran, published by Springer, New York, USA, (1981).

The present invention relates to a new ansamycin, called naphthomycin H, and to a process for its preparation from a microorganism called Streptomyces Y-8340369 (DSM 3278).

It has been possible to assign the following structural formula I to the compound according to the invention:

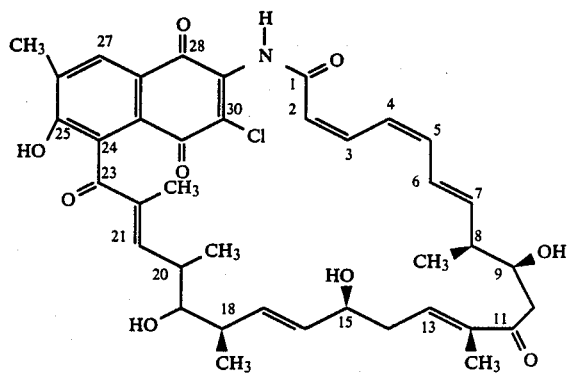

The microorganism for the production of naphthomycin H has been identified as a Streptomyces species from the order of Actinomycetales and from the family of Streptomycetaceae and the genus Streptomyces. The microorganism is described as Streptomyces echinatus Y-8340369 in the present invention. It was deposited at the German collection of microorganisms under receipt no. 3278 on Mar. 22, 1985.

The process for the preparation of the new ansamycin antibiotic called napththomycin H comprises cultivation of Streptomyces Y-8340369 (DSM 3278) by fermentation under aerobic conditions in a nutrient medium which contains sources of carbon and nitrogen, mineral nutrient salts and trace elements, and the antibiotic which is thus formed being isolated and purified in a known manner, as described below, from the culture broth.

Suitable sources of carbon are glucose, sucrose, starch, glycerol, dextrin, fructose, molasses, oatmeal, maltose, lactose or galactose, preferably glucose, starch, dextrin and mannitol. Sources of nitrogen which can be used are soybean meal, yeast meal, yeast extract, meat extract, malt extract, cornsteep liquor, peptone, casein, cottonseed oil or inorganic substances such as ammonium salts or nitrates (for example ammonium sulfate, sodium nitrate, ammonium chloride or potassion nitrate). Malt extract, yeast extract, soybean meal, peptone and cornsteep liquor are preferably used. Suitable inorganic nutrient salts are sodium chloride, magnesium sulfate, potassium chloride, potassium hydrogen phosphate and potassium dihydrogen phosphate, calcium chloride, calcium carbonate, ammonium hydrogen phosphate, sodium hydrogen phosphate, sodium hydrogen phosphate and sodium dihydrogen phosphate, magnesium phosphate or calcium phosphate. Trace elements which can be used are iron, manganese, copper, zinc or cobalt salts, or salts of other heavy metals. The cultivation of Streptomyces Y-8340369 can, where appropriate, be carried out in the presence of one or more antifoam agent(s), such as silicone or Desmophen[R].

The cultivation of Streptomyces Y-8340369 can be carried out at temperatures of 24°–40° C. at a pH of 6.0 to 8.0, preferably under aerobic conditions at 27° C. and pH 6.8.

Fermentation is stopped after 40–66 hours when the yield of the compound according to the invention is optimal. It is possible and preferable for the fermentation to be a submerged fermentation. The antifoam agent can be added at the start of the fermentation so that it is present in the culture broth at a concentration of 0.025%.

The progress of the fermentation and the formation of naphthomycin H of the present invention can be followed by measurement of the antibacterial activity, against *Staphylococcus aureus* 209P, of the culture broth.

The naphthomycin H is located both in the mycelium and in the culture filtrate of the resulting culture broth.

The naphthomycin H is isolated and purified in a known manner from the culture broth. Thus, it is possible to extract naphthomycin H from the culture fitrate using a solvent which is insoluble in water, such as ethyl acetate, chloroform or butanol, after the pH of the filtrate has been adjusted to 6.5–7.5. The preferred solvent is ethyl acetate, and the preferred pH is pH 7.0. The compound according to the invention is extracted from the mycelium by extraction of the mycelium, which has been obtained by filtration or centrifugation, with solvents such as ethyl acetate, chloroform, methanol, ethanol, acetone, butanol or methyl ethyl ketone, or with acidic solutions such as hydrochloric acid solution or acetic acid solution. The preferred solvent is acetone. After the extraction, the solvent is removed, for example by evaporation in vacuo, and the aqueous layer is adjusted to pH 6.5–7.5 and is extracted with a solvent such as ethyl acetate. The pH is preferably adjusted to 7.0. The solvent extracts of the culture filtrate and the mycelium are combined, evaporated to dryness and purified by, for example, column chromatography.

It is also possible to subject the culture broth as such to the solvent extraction employed for the mycelium, without previous removal of the mycelium, for isolation of the naphthomycin H.

Another method of obtaining naphthomycin H from the culture broth is based on adsorption. This entails the liquid substance, for example the culture filtrate or the solvent extracts containing the compound according to the invention, being treated by column chormatography or liquid chormatography etc., using suitable adsorbents, such as active charcoal, Diaion HP-20 ®, XAD ®, alumina, silica gel or Sephadex LH-20 ®. The compound according to the invention is eluted from the adsorbents using appropriate mobile phases, such as methanol or acetone, and the eluates are evaporated to dryness and purified by, for example, column chromatography. The purification can also be carried out, where appropriate, by countercurrent partition, preparative thin-layer chromatography and crystallization. Further purification can be effected by highpressure liquid chromatography.

The invention is illustrated in detail by the examples which follow:

EXAMPLE I

Cultivation of Streptomyces Y-8340369 (DSM 3278) for the preparation of naphthomycin H by fermentation Streptomyces Y-8340369 (DSM 3278) was added to a yeast-malt agar nutrient medium of the following composition:

| | |
|---|---|
| Malt extract | 10.0 g |
| Yeast extract | 4.0 g |
| Glucose | 4.0 g |
| Agar | 15.0 g |
| Distilled water | 1 l |
| pH | 7.0 |

The medium was distributed over test tubes and sterilized at 121° C. for 20 minutes. The tubes were then cooled in a slanting position to prepare agar slants, inoculated with the Streptomyces Y-8340369 culture isolated from soil, and incubated at 28° C. for 10–15 days until good growth and good sporulation were found. Five 500 ml Erlenmeyer flasks, each containing 100 ml of inoculation medium, or one 5 l suction flask containing 1 of inoculation culture medium were or was then inoculated with a suspension of spores, in distilled water, from a slant.

| Composition of the inoculation culture medium: | |
|---|---|
| Glucose | 15.0 g |
| Soybean meal | 15.0 g |
| Cornsteep liquor | 5.0 g |
| $CaCO_3$ | 2.0 g |
| NaCl | 5.0 g |
| Distilled water | 1 l |
| pH | 7.0 |

Then 100 ml portions of inoculation culture medium were distributed over 500 ml Erlenmeyer flasks, or 1 l of inoculation culture medium was placed in a 5 l suction flask, and sterilization was carried out at 121° C. for 20 minutes. The flasks or flask were (was) cooled, inoculated with the suspension of spores, and shaken at 240 rpm and at 28° C. for 72 hours in an orbital shaker with an amplitude of 3.75 cm. The grown culture was used as inoculum for a 15 l glass fermenter, containing 10 l of a 10% by volume inoculation culture medium, for the preparation of an inoculation culture for the second stage. The fermentation was carried out at 27° C. (±1° C.), while stirring at 160–180 rpm with an aeration rate of 0.6–0.8 VVM for 25 hours. The well-grown second-stage inoculation culture thus obtained was used as inoculum for the production medium.

| Composition of the production medium | |
|---|---|
| Starch | 10.0 g |
| Glucose | 10.0 g |
| Malt extract | 7.5 g |
| Peptone | 3.0 g |
| NaCl | 1.0 g |
| $MgSO_4.7H_2O$ | 1.0 g |
| $CuSO_4.5H_2O$ | 7.0 mg |
| $FeSO_4.7H_2O$ | 1.0 mg |
| $MnCl_2.4H_2O$ | 8.0 mg |
| $ZnSO_4.7H_2O$ | 2.0 mg |
| Distilled water | 1 l |
| pH | 7.0 |

0.025% Desmophen ® was added to the batches in the fermenters. 100 l of the production medium were introduced into a 150 l fermenter. The medium was sterilized by indirect and direct steam at 121° C. for 28 minutes. The fermenter was cooled and inoculated with the second-stageinoculation culture (10% V/V). The fermentation was carried out at 27° C. (±0.5° C.) while stirring at 120–140 rpm and with an aeration rate of 0.6–0.8 VVM for 66 hours. When the fermentation was stopped after 66 hours, the pH of the culture broth was 6.44 and the packed cell volume was 18 ml in 100 ml.

EXAMPLE II

Cultivation of Streptomyces Y-8340369 (DSM 3278) for the preparation of naphthomycin H by fermentation As example I, apart from the following differences:

| Composition of the agar medium | |
|---|---|
| Oatmeal | 20.0 g |
| Agar | 15.0 g |
| $FeSO_4.7H_2O$ | 0.1 mg |
| $ZnSO_4.7H_2O$ | 0.1 mg |
| $MnCl_2.4H_2O$ | 0.1 mg |
| Distilled water | 1 l |
| pH | 7.2 |

| Composition of the production medium | |
|---|---|
| Starch | 10.0 g |
| Glucose | 10.0 g |
| Soybean meal | 15.0 g |
| $K_2HPO_4$ | 1.0 g |
| $MgSO_4.7H_2O$ | 1.0 g |
| NaCl | 3.0 g |
| $CuSO_4.5H_2O$ | 7.0 mg |
| $FeSO_4.7H_2O$ | 1.0 mg |
| $MnCl_2.4H_2O$ | 8.0 mg |
| $ZnSO_4.7H_2O$ | 2.0 mg |
| Distilled water | 1 l |
| pH | 7.0 |

When the fermenter was harvested, the pH of the culture broth was 6.35 and the packed cell volume was 25 ml in 100 ml.

EXAMPLE III

Cultivation of Streptomyces Y-8340369 (DSM 3278) for the preparation of naphthomycin H by fermentation As example I, apart from the following differences:

| Composition of the culture medium | |
|---|---|
| Starch | 30.0 g |
| Sucrose | 10.0 g |
| Glucose | 10.0 g |
| Soya peptone | 15.0 g |
| Cornsteep liquor | 10.0 g |
| $K_2HPO_4$ | 3.0 g |
| NaCl | 1.0 g |
| $CaCO_3$ | 3.0 g |
| $CuSO_4.5H_2O$ | 7.0 g |
| $FeSO_4.7H_2O$ | 1.0 mg |
| $MnCl_2.4H_2O$ | 8.0 mg |
| $ZnSO_4.7H_2O$ | 2.0 mg |
| Distilled water | 1 l |
| pH | 7.2 |

| Composition of the production medium | |
|---|---|
| Dextrin | 20.0 g |
| Soybean meal | 10.0 g |
| Yeast extract | 2.0 g |
| $FeSO_4.7H_2O$ | 0.1 g |
| Distilled water | 1 l |
| pH | 7.0 |

When the fermenter was harvested, the pH of the culture broth was 6.73 and the packed cell volume was 24 ml in 100 ml.

EXAMPLE IV

Cultivation of Streptomyces Y-8340369 (DSM 3278) for the preparation of naphthomycin H by fermentation As example I, apart from the following differences:

| Composition of the inoculation culture medium: | |
|---|---|
| Glucose | 30.0 g |
| Soybean meal | 30.0 g |
| Cornsteep liquor | 10.0 g |
| $CaCO_3$ | 5.0 g |
| Distilled water | 1 l |
| pH | 7.0 |

| Composition of the production medium: | |
|---|---|
| Mannitol | 20.0 g |
| Soybean meal | 20.0 g |
| Distilled water | 1 l |
| pH | 7.2 |

When the fermenter was harvested after 54 hours, the pH of the culture broth was 6.46 and the packed cell volume was 18 ml in 100 ml.

EXAMPLE V

Cultivation of Streptomyces Y-8340369 (DSM 3278) for the preparation of naphthomycin H by fermentation As example I, apart from the following differences:

| Composition of the inoculation culture medium: | |
|---|---|
| Soybean meal | 15.0 g |
| Starch | 15.0 g |
| Glucose | 50.0 g |
| $CaCO_3$ | 10.0 g |
| $CoCl_2.6H_2O$ | 5.0 g |
| Distilled water | 1 l |
| pH | 7.0 |

| Composition of the production medium: | |
|---|---|
| Soluble starch | 20.0 g |
| Glucose | 15.0 g |
| Soya peptone | 3.0 g |
| Peptone | 3.0 g |
| $CaCO_3$ | 2.0 g |
| Cornsteep liquor | 2.0 g |
| NaCl | 2.0 g |
| $(NH_4)_2SO_4$ | 0.5 g |
| $CuSO_4.5H_2O$ | 7 0 g |
| $FeSO_4.7H_2O$ | 1.0 g |
| $MnCl_2.4H_2O$ | 8.0 g |
| $ZnSO_4.7H_2O$ | 2.0 g |
| Distilled water | 1 l |

-continued

| Composition of the production medium: | |
|---|---|
| pH | 6.7 |

When the fermenter was harvested after 48 hours, the pH was 6.78 and the packed cell volume was 18 ml in 100 ml.

EXAMPLE VI

Isolation, purification and identification of naphthomycin H

About 90 l of fermentation broth were centrifuged to separate mycelium and culture filtrate. The resulting culture filtrate (90 l) was adjusted to a pH of 7.0 with 2N NaOH and was extracted twice with 30 l of ethyl acetate. The aqueous layers were discarded, and the combined ethyl acetate extracts were evaporated to dryness in vacuo. The resulting crude extract amounted to about 35.8 g. The resulting mycelium (3.9 kg) was extracted three times with 15 l of acetone each time. The combined extracts were evaporated in vacuo to remove the acetone. The resulting aqueous layer was adjusted to a pH of 7.0 with 2N NaOH, and was extracted twice with 5 l of ethyl acetate. The aqueous layers were discarded, and the combined extracts were evaporated to dryness in vacuo. About 16.0 g of crude extract were obtained.

36 g of crude extract were applied to a 3.5×49 cm silica gel column, and eluted successively with chloroform and a chloroform:methanol mixture in which the methanol concentration gradually rose to 5% (final composition 95:5). In this way, 14.6 g of semi-pure compound were obtained, and this was applied to a silica gel (200-300 mesh) column 6×31 cm in size, and was then eluted with a benzene:ethyl acetate mixture gradually increasing the ethyl acetate concentration to 60% (final composition 4:6). This resulted in fraction A in an amount of about 0.19 g and fraction B in an amount of about 1.2 g. For further purification, fraction A was applied to a 1.4×80 cm Sephadex LH 20 ® column and was eluted with methanol, resulting in 142 mg of a compound which was purified by preparative thin-layer chromatography (silica gel plates of thickness 0.5 mm) in a mixture of chloroform:methanol (95:5). This resulted in 96 mg of a pure compound which was identified as the known antibiotic naphthomycin A. Then a 6×30 cm silica gel H ® column (without binder) was charged, as a chromatography column, with fraction B, and elution was carried out with a mixture of chloroform and methanol (96:4). This resulted in 650 mg of a semi-pure substance which was purified by a preparative thin-layer chromatography (silica gel plates 1 mm thick) in a mixture of chloroform and methanol (95:5), and was then recrystallized from a petroleum ether:benzene:ethyl acetate mixture, this resulting in naphthomycin H in an amount of 120 mg.

The naphthomycin H was identified by chemical analysis and by spectroscopic methods.

A concentration of 10 mg/l was used to determine the UV absorption maxima of naphthomycin H. The absorption spectrum was measured in the range 200 to 800 nm.

The $^1$H and $^{13}$C nuclear magnetic resonance spectra were determined in CDCl$_3$ using a Bruker HX-270 Fourier-transform nuclear magnetic resonance spectrometer at 270 MHz.

The IR spectrum in nujol was determined using a Perkin Elmer P.E.683 IR spectrometer, and that in KBr was determined using a Perkin Elmer P.E. 521 IR spectrometer.

The mass spectrum was measured using a AEI MS-902S mass spectrometer using a FAB (fast atom bombardment) ion source.

Physicochemical properties of naphthomycin H: Appearance: pale yellow crystalline powder; Chemical formula: $C_{39}H_{44}ClNO_9$; Molecular weight: 705 (FAB MS: M+H$^+$=706); [α]$_D$: +302.93° (c 1.7,CHCl$_3$); Melting point: 150° C. (decomposition).

UV spectrum: λmax. in (a) methanol: 228, 302 nm; (b) 0.1N NaOH/methanol: 216, 236 (sh), 298, 428 nm; (c) 0.1N NaOH: 240, 298, 425 nm.

IR spectra: (a) in KBr, C=O region: 1667, 1626, 1600 and 1577 cm$^{-1}$; (b) in nujol.

NMR spectra:

The signals of the olefinic protons which do not belong to the triene system are assigned as follows: the two doublets of doublets at 5.47 and 5.63 ppm belong to a trans-disubstituted double bond ($J_{16,17}$=15 Hz). The doublet at 5.93 ppm shows long-range coupling with a methyl group (2.02 ppm, J~1.5 Hz) and vicinal coupling with a methine proton (2.7 ppm, J=10 Hz) and is thus assigned to HC(21). The signal for HC(13) appears as a broadened triplet at 6.72 ppm. The coupling constants of the triene system in naphthomycin H ($J_{2,3}$=11.5, $J_{4,5}$=11, $J_{6,7}$=15 Hz) show that C(2)=C(3) and C(4)+C(5) have Z geometry, whereas the other double bond C(6)—C(7) has E geometry (cf. the structure of naphthomycin H in Formula I).

TABLE I $^1$H NMR decoupling experiments on naphthomycin H (270 MHz, CDCl$_3$)$^{(a),(b)}$

| Irradiation [ppm] | Observed signal δppm H (X) | Converted into/ J (Hz)$^{(c)}$ | Assignment H (X) |
|---|---|---|---|
| HC(3) [6.98] | 6.32 dd (1H) | d/~11 | HC(4) |
| | 6.04 d (1H) | s | HC(2) |
| HC(13) [6.72] | 2.32 m (2H) | u | H$_2$C(14) |
| | 1.72 d (3H) | s | H$_3$C—C(12) |
| HC(6) [6.52] | 6.32 dd (1H) | d/~11 | HC(5) |
| | 5.54 dd (1H) | d/~10 | HC(7) |
| HC(2) [6.04] | 6.95 dd (1H) | d/11 | HC(3) |
| HC(21) [5.94] | 2.70 m (1H) | dq/3.7 | HC(20) |
| | 2.04 d (3H) | s | H$_3$C—C(22) |
| HC(15) [4.04] | 5.62 dd (1H) | d/15 | HC(16) |
| | 2.32 m (2H) | u | H2C(14) |
| HC(9) [3.57] | 3.14 dd (1H) | d/17 | } H$_2$C(10) |
| | 2.62 dd (1H) | d/17 | |
| | 2.32 m (1H) | u | HC(8) |
| H$_3$C—C(8) [1.22] | 2.32 m (1H) | u | HC(8) |
| H$_3$C—C(18) [0.97] | 2.22 m (1H) | dd/10 + 10 | HC(18) |
| H$_3$C—C(20) [0.82] | 2.70 m (1H) | dd/3 + 10 | CH (20) |

$^{(a)}$coupling constants in Hz: 2/3 = 11.5; 3/4 = 11; 4/5 = 11; 6/7 = 15; 10 a/b = 17; 16/15 = 7.5; 21/20 = 10; 22 CH$_{3/21}$ = 1.5.
$^{(b)}$There are 5 exchangeable protons 2.65 (OH), 3.65 (2 × OH), 8.0 (S, NH), 9.78 (HO—C(25))
$^{(c)}$u = type of signal not entirely distinct because of incomplete decoupling.

The presence of 39 carbon atoms in naphthomycin H is verified in Table II below.

TABLE II $^{13}$C NMR of naphthomycin H in CDCl$_3$ (67.9 MHz) in ppm

| | |
|---|---|
| C=O region: | ketone carbon atoms 203.5; 201.6 |
| | quinone carbon atoms 178.6; 178.1 |
| | amide carbon atoms 165.0 |
| sp$^2$ region: | 161.2; 147.2; 142.5; 141.6; 138.0; 137.6; |
| | 136.8; 136.7; 135.9; 135.5; 134.5; 133.8; |

TABLE II-continued

| $^{13}C$ NMR of naphthomycin H in $CDCl_3$ (67.9 MHz) in ppm | |
|---|---|
| | 133.3; 132.5; 131.2; 126.5; 123.4; 121.4; 121.0; 119.9 |
| $sp^3$ region: | (CH—O, CH—, $CH_2$—, $CH_3$—): 76.3; 73.3; 71.8; 45.2; 41.7; 40.6; 36.4; 33.7; 17.4; 16.4; 16.2; 12.4; 11.2; 10.8 |

Solubility: Soluble in methanol, acetone, ethyl acetate and chloroform and slightly soluble in hexane, petroleum ether and aqueous alkali. TLC (thin-layer chromatography) data: naphthomycin H has the $R_f$ values shown in Table III below (determined by comparison with other naphthomycins on silica gel layers using various solvent systems).

TABLE III

TLC data using 0.2 mm silica gel 60 $F_{254}$ (Merck) layers on aluminum foil.

| | $R_f$ value Naphthomycin | | |
|---|---|---|---|
| Solvent system | A | B | C |
| EtOAc | 0.64 | 0.53 | 0.46 |
| EtOAc:MeOH (98.2) | 0.48 | 0.44 | 0.41 |
| Benzene:EtOAc (2:8) | 0.56 | 0.38 | 0.28 |
| EtOAc:acetic acid (200:1) | 0.57 | 0.47 | 0.41 |
| EtOAcH$_2$O:formic acid (100:30:2.5, upper phase) | 0.74 | 0.64 | 0.63 |

It is evident from the above results in association with the fragmentation pattern in the mass spectrometer that the new compound having antibiotic activity, naphthomycin H, has the structure shown in Formula I.

The antimicrobial activity of naphthomycin H was determined in comparison with that of naphthomycins A and B. The results are reported as zone diameter (in millimeters) of the zone of inhibition produced by the presence of naphthomycin compound in the form of 1 mg/ml solution on a 6 mm filter paper disc on agar which contains the test organism in Table IV below.

TABLE IV

| | Zone diameter (mm) Naphthomycin (1 mg/ml) | | |
|---|---|---|---|
| Microorganism | H | A | B |
| Staphylococcus aureus 209 P | 17 | 14 | 15 |
| Streptococcus faecalis | 12 | 9 | 10 |
| Sarcina lutea | 18 | 12 | 16 |
| Bacillus subtilis | 15 | 9 | 12 |

TABLE IV-continued

| | Zone diameter (mm) Naphthomycin (1 mg/ml) | | |
|---|---|---|---|
| Microorganism | H | A | B |
| Alcaligenes faecalis | 12 | — | 10 |
| Candida albicans | 18 | 11 | 16 |
| Penicillium italicum | 16 | 14P | 15 |
| Aspergillus niger | 17/21 | 13 | 14/18 |
| Saccharomyces cerevisiae | 10 | — | 10 |
| Fusarium nivale | 15 | — | 20 |

P = partial zone

Thus, naphthomycin H is active against Gram-positive bacteria and fungi and can be used as an antibiotic for the treatment of fungal and staphylococcal infections.

For use of the compound according to the invention as an antibiotic, a suitable dose unit is 12.5–50 mg/kg (p.o.) and a suitable daily dose is as follows:
1st day (2x) 25–100 mg/kg (p.o.)
2nd day (1x) 12.5–50 mg/kg (p.o.)

For topical use against fungal infections, ointments or solutions containing 10–20 mg/ml are used, for example.

What is claimed is:

1. Naphthomycin H of the formula I

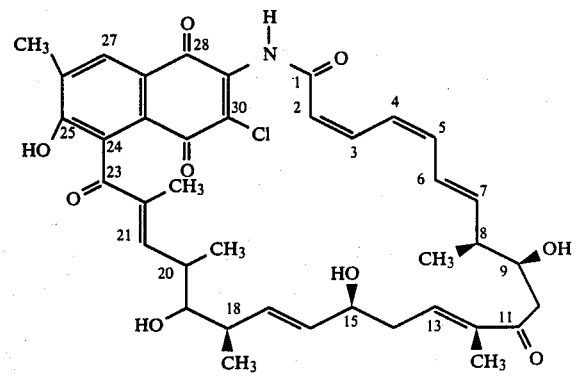

2. A pharmaceutical composition for use as an antibiotic comprising an effective amount of the compound as defined in claim 1 in association with a pharmaceutically acceptable carrier.

3. A method of treating a patient in need of an antibiotic which comprises administering to said patient an effective amount of the compound as defined in claim 1 in association with a pharmaceutically acceptable carrier.

* * * * *